United States Patent
Auger et al.

(10) Patent No.: US 8,618,301 B2
(45) Date of Patent: Dec. 31, 2013

(54) 5-PHENYLPYRAZOLOPYRIDINE DERIVATIVES, PREPARATION AND THERAPEUTIC USE THEREOF

(75) Inventors: Florian Auger, Paris (FR); Danielle De Peretti, Paris (FR); Luc Even, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/496,118

(22) PCT Filed: Sep. 17, 2010

(86) PCT No.: PCT/FR2010/051932
§ 371 (c)(1),
(2), (4) Date: Oct. 5, 2012

(87) PCT Pub. No.: WO2011/033230
PCT Pub. Date: Mar. 24, 2011

(65) Prior Publication Data
US 2013/0023554 A1    Jan. 24, 2013

(30) Foreign Application Priority Data
Sep. 18, 2009  (FR) ..................... 09 56444

(51) Int. Cl.
*C07D 491/02* (2006.01)
*C07F 5/02* (2006.01)

(52) U.S. Cl.
USPC ............................................ 546/121; 549/13

(58) Field of Classification Search
USPC ..................... 546/121, 13; 514/300
See application file for complete search history.

(56) References Cited

U.S. PATENT DOCUMENTS

2008/0207902 A1    8/2008  Kohno et al.

FOREIGN PATENT DOCUMENTS

| FR | 2 925 900 A1 | 7/2009 |
| WO | WO03/078435 A1 | 9/2003 |
| WO | WO2008/078091 A1 | 7/2008 |

OTHER PUBLICATIONS

Schweizer et al. Journal of Organic Chemistry, 1987, 52, 1319-1324.*
Schweizer, Edward E. et al., "Reactions of Azines. 9. Preparation of 4,5-Dihydropyrazolo[1,5-a]pyridines, 6,7-Dihydropyrazolo[1,5-a]pyridines, and Pyrazolo[1,5-a]pyridines," Journal of Organic Chemistry (1987), vol. 52, pp. 1319-1324.
International Search Report dated Dec. 3, 2010 issued in PCT/FR2010/051932.

* cited by examiner

*Primary Examiner* — Nizal Chandrakumar
(74) *Attorney, Agent, or Firm* — Scully, Scott, Murphy & Presser, P.C.

(57) ABSTRACT

The present invention relates to compounds of formula (I).

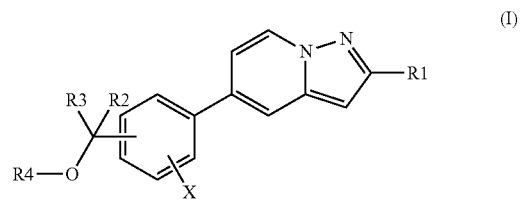

7 Claims, No Drawings

5-PHENYLPYRAZOLOPYRIDINE DERIVATIVES, PREPARATION AND THERAPEUTIC USE THEREOF

The present invention relates to 5-phenylpyrazolopyridine derivatives, to their preparation and to their therapeutic application in the treatment or prevention of diseases involving Nurr-1 nuclear receptors, also known as NR4A2, NOT, TINUR, RNR-1 and HZF3.

A subject-matter of the present invention is the compounds of formula (I):

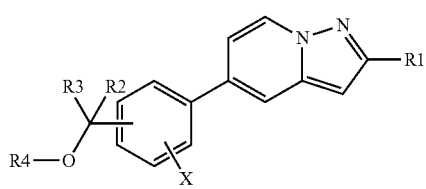

in which:
R1 represents:
 a phenyl group or a naphthyl group, it being possible for these two groups optionally to be substituted by one or more atoms or groups chosen, independently of one another, from the following atoms or groups: halogen, $(C_1-C_6)$alkyl, halo$(C_1-C_6)$alkyl, $(C_1-C_6)$alkoxy, halo$(C_1-C_6)$alkoxy, $(C_1-C_6)$thioalkyl, —S(O)$(C_1-C_6)$alkyl, —S(O)$_2$$(C_1-C_6)$alkyl, hydroxyl, hydroxy$(C_1-C_6)$alkylene, CHO, COOH, $(C_1-C_6)$alkoxy$(C_1-C_6)$alkyleneoxy, NRaRb, CONRaRb, SO$_2$NRaRb, NRcCORd, OC(O)NRaRb, OCO$(C_1-C_6)$alkyl, NRcC(O)ORe or NRcSO$_2$Re,
X represents from 1 to 4 substituents which are identical to or different from one another and which are chosen from hydrogen, halogen, $(C_1-C_6)$alkyl or $(C_1-C_6)$alkoxy, it being possible for the $(C_1-C_6)$alkyl group to be optionally substituted by one or more groups chosen from a halogen, $(C_1-C_6)$alkoxy or hydroxyl;
R2 and R3 represent, independently of one another,
 a hydrogen atom,
 a $(C_1-C_6)$alkyl group optionally substituted by an Rf group;
 a CHO or COOH group,
X and R3 can together form, with the carbon atoms which carry them, a carbocycle of 5 to 7 carbon atoms;
R4 represents a hydrogen atom or a $(C_1-C_6)$alkyl group,
Ra and Rb represent, independently of one another, a hydrogen atom or a $(C_1-C_6)$alkyl, aryl$(C_1-C_6)$alkylene or aryl group;
or Ra and Rb together form, with the nitrogen atom which carries them, an azetidine, pyrrolidine, piperidine, azepine, morpholine, thiomorpholine, piperazine or homopiperazine group, this group being optionally substituted by a $(C_1-C_6)$alkyl, aryl or aryl$(C_1-C_6)$alkylene group;
Rc and Rd represent, independently of one another, a hydrogen atom or a $(C_1-C_6)$alkyl, aryl$(C_1-C_6)$alkylene or aryl group;
or Rc and Rd together form a $(C_2-C_5)$alkylene group;
Re represents a $(C_1-C_6)$alkyl, aryl$(C_1-C_6)$alkylene or aryl group;
or Rc and Re together form a $(C_2-C_5)$alkylene group;
Rf represents a hydroxyl, oxo, CHO or COOH group,
in the form of the base or of an addition salt with an acid.

The compounds of formula (I) can comprise one or more asymmetric carbon atoms. They can thus exist in the form of enantiomers or diastereoisomers. These enantiomers and diastereoisomers, and their mixtures, including the racemic mixtures, come within the invention.

The compounds of formula (I) can exist in the form of bases or of addition salts with acids. Such addition salts come within the invention.

These salts can be prepared with pharmaceutically acceptable acids but the salts of other acids, for example of use in the purification or the isolation of the compounds of formula (I), also come within the invention.

The compounds of formula (I) can also exist in the form of hydrates or solvates, namely in the form of combinations or associations with one or more molecules of water or with a solvent. Such hydrates and solvates also come within the invention.

In the context of the present invention:
 a $(C_x-C_t)$ group is understood to mean a group comprising between x and t carbon atoms;
 a halogen atom is understood to mean a fluorine, a chlorine, a bromine or an iodine;
 an alkyl group is understood to mean a saturated, linear, branched or cyclic, aliphatic group optionally substituted by a saturated, linear, branched or cyclic, alkyl group. Mention may be made, by way of examples, of the methyl, ethyl, propyl, isopropyl, butyl, isobutyl, tert-butyl, cyclopropyl, cyclobutyl, cyclopentyl, cyclohexyl, methylcyclopropyl or cyclopropylmethyl groups, and the like;
 an alkylene group is understood to mean a divalent alkyl group;
 an alkoxy group is understood to mean an —O-alkyl radical where the alkyl group is as defined above;
 a haloalkyl group is understood to mean an alkyl group substituted by one or more identical or different halogen atoms. Mention may be made, by way of examples, of the CF$_3$, CH$_2$CF$_3$, CHF$_2$ or CCl$_3$ groups;
 a haloalkoxy group is understood to mean an —O-alkyl radical where the alkyl group is as defined above and is substituted by one or more identical or different halogen atoms. Mention may be made, by way of examples, of the OCF$_3$, OCHF$_2$ or OCCl$_3$ groups;
 a thioalkyl group is understood to mean an S-alkyl radical where the alkyl group is as defined above;
 the sulphur and nitrogen atoms can be in the oxidized state (N-oxide, sulphoxide, sulphone);
 an aryl group is understood to mean a mono- or bicyclic aromatic group comprising from 6 to 10 atoms. Mention may be made, by way of examples of aryl groups, of phenyl and naphthyl;
 a carbocycle is understood to mean a saturated, partially saturated or unsaturated and mono- or bicyclic group comprising from 5 to 7 carbon atoms. Mention may be made, by way of examples of carbocycles, of indane.

Among the compounds of formula (I) which are subject-matters of the invention, a first group of compounds is composed of the compounds in which:
R1 represents a phenyl group substituted by a halogen;
R2 and R3 represent, independently of one another, a hydrogen atom or a $(C_1-C_6)$alkyl group,
R4 represents a hydrogen atom or a $(C_1-C_6)$alkyl group;
X represents one or more hydrogen or halogen atoms, or X and R3 can form, together with the carbon atoms which carry them, a carbocycle of 5 carbon atoms;
in the form of the base or of an addition salt with an acid.

Among the compounds of formula (I) which are subject-matters of the invention, a second group of compounds is composed of the compounds in which:
R1 represents a phenyl group substituted by a chlorine or fluorine atom;
R2 and R3 represent, independently of one another, a hydrogen atom, a methyl or a cyclopropyl group;
R4 represents a hydrogen atom or a methyl group;
X represents one or more hydrogen or fluorine atoms, or X and R3 can form, together with the carbon atoms which carry them and with the benzofused ring, an indane group, in the form of the base or of an addition salt with an acid.

Mention may in particular be made, among the compounds of formula (I) which are subject-matters of the invention, of the following compounds:
 {3-[2-(4-Chlorophenyl)pyrazolo[1,5-a]pyridin-5-yl]phenyl}methanol
 2-{3-[2-(4-Chlorophenyl)pyrazolo[1,5-a]pyridin-5-yl]phenyl}propan-2-ol
 1-{3-[2-(4-Chlorophenyl)pyrazolo[1,5-a]pyridin-5-yl]phenyl}ethanol
 1-{3-[2-(4-Chlorophenyl)pyrazolo[1,5-a]pyridin-5-yl]phenyl}cyclopropylmethanol
 {3-[2-(4-Chlorophenyl)pyrazolo[1,5-a]pyridin-5-yl]-2,6-difluorophenyl}methanol
 {3-[2-(4-Fluorophenyl)pyrazolo[1,5-a]pyridin-5-yl]phenyl}methanol
 2-{3-[2-(4-Fluorophenyl)pyrazolo[1,5-a]pyridin-5-yl]phenyl}propan-2-ol
 1-{3-[2-(4-Fluorophenyl)pyrazolo[1,5-a]pyridin-5-yl]phenyl}ethanol
 2-(4-Chlorophenyl)-5-(3-methoxymethylphenyl)pyrazolo[1,5-a]pyridine
 {4-[2-(4-Chlorophenyl)pyrazolo[1,5-a]pyridin-5-yl]phenyl}methanol
 {2-[2-(4-Chlorophenyl)pyrazolo[1,5-a]pyridin-5-yl]phenyl}methanol
 6-[2-(4-Chlorophenyl)pyrazolo[1,5-a]pyridin-5-yl]indan-1-ol In accordance with the invention, the compounds of general formula (I) can be prepared according to the process described in Scheme 1.

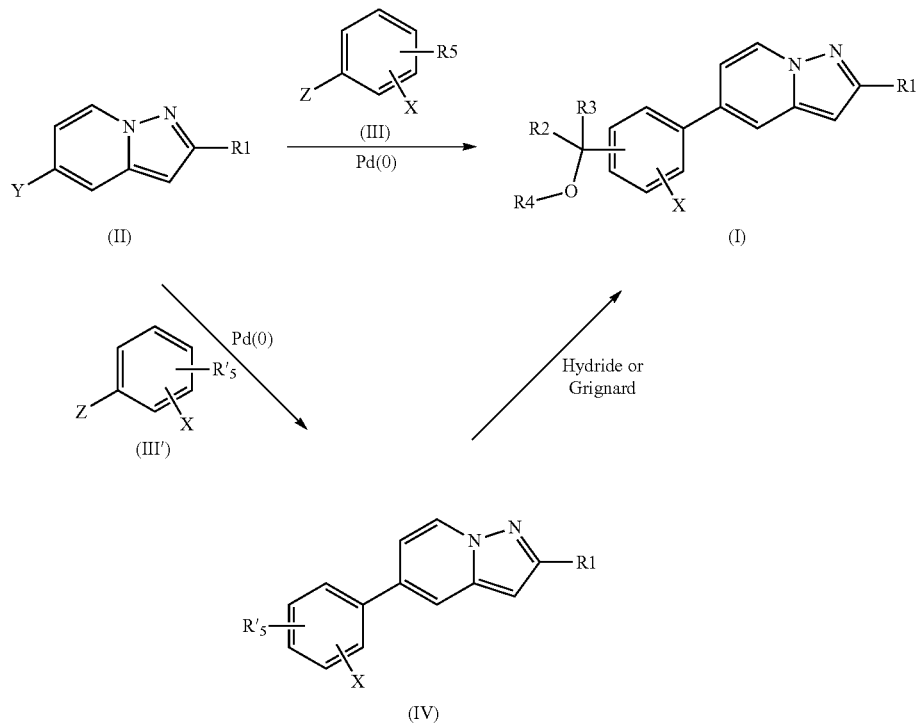

The compounds of the invention can be prepared according to Scheme 1 by a coupling reaction, catalysed by a metal, such as palladium, between a pyrazolopyridine of general formula (II), in which R1 is defined as above and Y represents a halogen atom or a boron derivative, and a derivative of general formula (III), in which X is defined as above, Z represents a boron or tin derivative if Y represents a halogen atom or else a halogen atom if Y represents a boron derivative, and R5 represents the

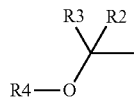

group, in order to obtain the compounds of general formula (I), for example, according to the method described by A. Gueiffier in *Helv. Chim. Acta,* 2001, 84, 3610-3615.

The compounds of the invention can also be prepared according to Scheme 1 by a coupling reaction, catalysed by a metal, such as palladium, between a pyrazolopyridine of general formula (II), in which R1 is defined as above and Y represents a halogen atom or a boron derivative, and a derivative of general formula (III') in which X is defined as above, Z represents a boron or tin derivative if Y represents a halogen atom or else a halogen atom if Y represents a boron derivative, and R5' represents a carbonyl derivative R2CO, in which R2 is defined as above, or else R5' represents an alkylcarboxylate or an aldehyde, in order to obtain the compounds of general formula (IV), for example, according to the method described by A. Gueiffier in *Helv. Chim. Acta,* 2001, 84, 3610-3615.

Subsequently, the compounds of general formula (IV) can be converted to compounds of general formula (I), for which R4 represents a hydrogen atom, by the action of an organometallic derivative, such as an organomagnesium derivative, for example R3MgBr, in which R3 is defined as above, or by reduction of the carbonyl group using a metal hydride, for example sodium borohydride or one of its derivatives, or any other method known to a person skilled in the art.

In accordance with the invention, the compounds of general formula (IIa) can be prepared according to the process described in Scheme 2.

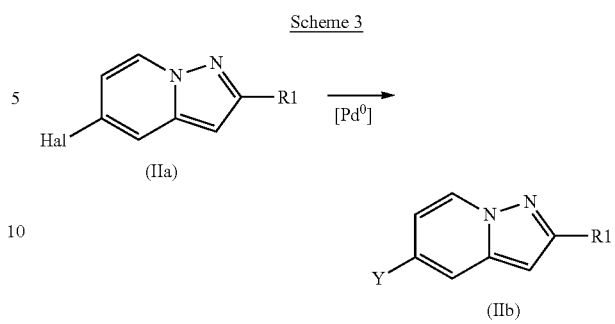

The compounds (IIb), in which Y represents a boron derivative, can be prepared according to Scheme 3 by a coupling reaction, for example of bis(pinacolato)diboron, on the compounds (IIa) catalysed by a metal, such as palladium,

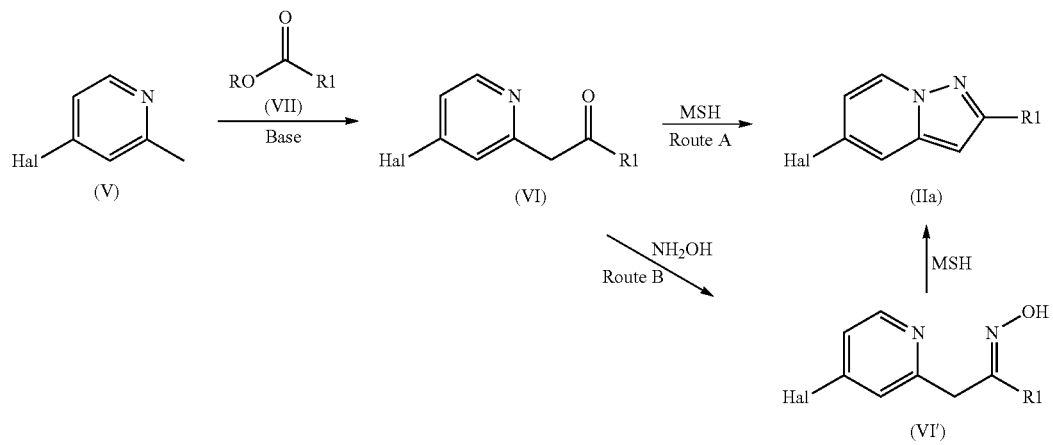

In Scheme 2, Route A, the compounds of general formula (IIa), in which R1 is defined as above and Hal represents a halogen atom, can be prepared by the action of O-(mesitylenesulphonyl)hydroxylamine (MSH) on a compound of general formula (VI), in which R1 and Hal are defined as above, for example according to the method described by Y. Tamura, J.-H. Kim, Y. Mild, H. Hayashi and M. Ikeda, in *J. Het. Chem.,* 1975, 12, 481.

In Scheme 2, Route B, the compounds of general formula (IIa), in which R1 is defined as above and Hal represents a halogen atom, can also be prepared by the action of O-(mesitylenesulphonyl)hydroxylamine on an oxime of general formula (VI'), in which R1 and Hal are defined as above, for example according to the method described by Y. Tamura, J.-H. Kim, Y. Mild, H. Hayashi and M. Ikeda, in *J. Het. Chem.,* 1975, 12, 481. The compounds (VI') can be obtained by the action of hydroxylamine on the compounds (VI).

The compounds (VI) can be obtained from the compounds (V) by the action of the esters of general formula (VII), in which R1 is defined as above and R represents an alkyl group, in the presence of a strong base, for example according to the method described by K. S. Gudmundsson in *Bioorg. Med. Chem.,* 2005, 13, 5346.

In accordance with the invention, the compounds of general formula (IIb) can also be prepared according to the process described in Scheme 3.

according to the method described by E. F. DiMauro and R. Vitullo, *J. Org. Chem.,* 2006, 71(10), 3959.

In Schemes 1, 2 and 3, the starting compounds and the reactants, when their method of preparation is not described, are commercially available or are described in the literature or else can be prepared according to methods which are described therein or which are known to a person skilled in the art.

According to another of its aspects, another subject-matter of the invention is the compounds of formula (IIb), in particular the compound of formula (IIb1). These compounds are of use as intermediates in the synthesis of the compounds of formula (I).

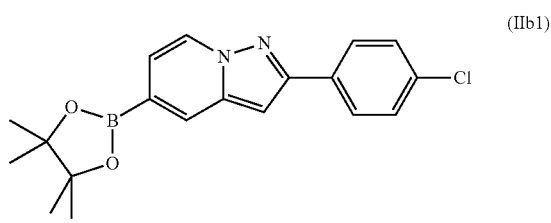 [SMILES: CC1(C)OB(c2ccn3nc(-c4ccc(Cl)cc4)cc3c2)OC1(C)C]

The following examples describe the preparation of certain compounds in accordance with the invention. These examples are not limiting and serve only to illustrate the present invention. The numbers of the compounds of the examples refer to those given in the table below, in which the chemical structures and physical properties of a few compounds according to the invention are illustrated.

EXAMPLE 1

{3-[2-(4-chlorophenyl)pyrazolo[1,5-a]pyridin-5-yl] phenyl}methanol (Compound 1 of the Table)

1.1 2-(4-bromopyridin-2-yl)-1-(4-chlorophenyl)ethanone 1.0 g (5.8 mmol) of 4-bromo-2-methylpyridine and 2.14 g (11.6 mmol) of ethyl 4-chlorobenzoate are placed under a stream of argon in a round-bottomed flask and dissolved in 10 ml of anhydrous tetrahydrofuran. The solution is cooled to 0° C. and 12 ml of a lithium hexamethyldisilazane (LiHMDS) solution (1M in tetrahydrofuran) are added. After addition, the mixture is heated at 45° C. for 3 h and cooled to ambient temperature, and then water is added. The tetrahydrofuran is subsequently evaporated under reduced pressure and the aqueous phase is extracted three times with ether. The organic phase is separated, dried and concentrated under reduced pressure. The residue obtained is purified by chromatography on silica gel, elution being carried out with a mixture of dichloromethane and heptane. 1.11 g (62%) of compound are obtained.

LC-MS: M+H=310

$^1$H NMR ($d_6$-DMSO) δ (ppm): 4.6 (s, 2H); 6.4 (s, 1H); 7.4 (s, 1H); from 7.5 to 7.6 (m, 6H); 7.7 (s, 1H); 7.9 (d, 2H); 8.1 (d,2H); 8.3 (d, 1H); 8.4 (d, 1H); 15.0 (s, 1H). (Keto/enol ratio: 43/57).

1.2 O-mesitylenesulphonylhydroxylamine 5.00 g (7.52 mmol) of ethyl O-(2-mesitylenesulphonyl) acetohydroxamate are placed in 3 ml of 1,4-dioxane in a round-bottomed flask. The mixture is cooled to 0° C. and 2 ml (23.20 mmol) of perchloric acid $HClO_4$ (70% in water) are added. The mixture is subsequently stirred at 0° C. for 15 minutes and ice-cold water is added thereto. A precipitate is formed, which precipitate is collected by filtration and washed with ice-cold water and with cold petroleum ether. 5.26 g of compound are obtained.

$^1$H NMR ($d_6$-DMSO) δ (ppm): 2.2 (s, 3H); 2.5 (s, 6H); 6.8 (s, 2H); 9.0 (s, 2H). M+H=216.

1.3 5-bromo-2-(4-chlorophenyl)pyrazolo[1,5-a]pyridine 705 mg (3.27 mmol) of O-mesitylenesulphonylhydroxylamine (compound obtained according to the protocol described in 1.2) are placed in a round-bottomed flask and dissolved in 10 ml of dichloromethane. The solution is cooled to 0° C. and a solution of 705 mg (2.27 mmol) of 2-(4-bromopyridin-2-yl)-1-(4-chlorophenyl)ethanone (compound obtained according to the protocol described in 1.1) in 14 ml of dichloromethane is added dropwise. After stirring at 0° C. for 1 hour and at ambient temperature for 6 hours, 150 mg of O-(mesitylsulphonyl)hydroxylamine in 3 ml of dichloromethane are added to the reaction mixture and stirring is carried out at ambient temperature for 16 h. 300 mg of O-(mesitylsulphonyl)hydroxylamine in 1 ml of dichloromethane are then again added to the mixture and the latter is left stirring at ambient temperature for 7 hours. A precipitate is formed, which precipitate is removed by filtration. The filtrate is then washed successively with water, with an aqueous sodium hydrogencarbonate solution and with a saturated sodium chloride solution, then dried over magnesium sulphate and concentrated under reduced pressure. The residue obtained is purified by chromatography on silica gel, elution being carried out with dichloromethane. 126 mg (18%) of compound are obtained.

LC-MS: M+H=307

$^1$H NMR ($d_6$-DMSO) δ (ppm): 7.0 (d, 1H); 7.1 (s, 1H); 7.6 (d, 2H); 8.0 (s, 1H); 8.1 (d, 2H); 8.7 (d, 1H).

1.4 {3-[2-(4-chlorophenyl)pyrazolo[1,5-a]pyridin-5-yl]phenyl}methanol (Compound No. 1)

126 mg (0.41 mmol) of 5-bromo-2-(4-chlorophenyl)pyrazolo[1,5-a]pyridine (compound obtained according to the protocol described in 1.3), 80 mg (0.53 mmol) of 3-(hydroxymethyl)phenylboronic acid and 24 mg (0.02 mmol) of tetrakis(triphenyl-phosphine)palladium are placed under a stream of argon in a round-bottomed flask containing a mixture of 4 ml of dimethoxyethane and 1 ml of an aqueous sodium carbonate solution (2M) degassed beforehand under a stream of argon. The reaction mixture is heated at 80° C. for 6 hours and then, after cooling, concentrated under reduced pressure. The residue is taken up in ethyl acetate and water and then the organic phase is separated, dried and concentrated under reduced pressure. The residue is purified by chromatography on silica gel, elution being carried out with a mixture of dichloromethane and methanol. The solid obtained is triturated from ethyl ether, collected by filtration and then dried in an oven under reduced pressure. 57 mg (41%) of compound are obtained.

Melting point (° C.): 161-164.

LC-MS: M+H=335

$^1$H NMR ($d_6$-DMSO) δ (ppm): 4.6 (d, 2H); 5.3 (t, 1H); 7.1 (s, 1H); 7.3 (d, 1H); 7.4 (d, 1H); 7.5 (t, 1H); 7.6 (d, 2H); 7.7 (d, 1H); 7.8 (s, 1H); 8.0 (s, 1H); 8.1 (d, 2H); 8.8 (d, 1H).

EXAMPLE 2

2-(4-chlorophenyl)-5-(3-methoxymethylphenyl)pyrazolo[1,5-a]pyridine (Compound 9 of the Table)

2.1 2-(4-bromopyridin-2-yl)-1-(4-chlorophenypethanone 5 g (29.07 mmol) of 4-bromo-2-methylpyridine and 11.27 g (61.04 mmol) of ethyl 4-chlorobenzoate are placed under a stream of nitrogen in a round-bottomed flask and dissolved in 50 ml of anhydrous tetrahydrofuran. The solution is cooled to 5° C. and 70 ml (70 mmol) of a lithium hexamethyldisilazane solution (1M in tetrahydrofuran) are added dropwise. After addition, the mixture is stirred at ambient temperature for 2 h and cooled to 5° C., and then 100 ml of water are gradually added. The medium is subsequently diluted with 250 ml of ethyl acetate and 100 ml of water. The organic phase is separated and the aqueous phase is extracted twice with 100 ml of ethyl acetate. The organic phases are subsequently combined, dried over sodium sulphate and filtered. 15 g of silica are subsequently added to the filtrate and the mixture is concentrated under reduced pressure. The powder obtained is used as solid deposit for chromatography on silica gel, with a mixture of cyclohexane and ethyl acetate (9/1) as eluent. 8.4 g (93%) of compound are obtained in the form of a yellow powder.

LC-MS: M+H=310

¹H NMR (d₆-DMSO) δ (ppm): 4.6 (s, 2H); 6.4 (s, 1H); 7.4 (s, 1H); from 7.5 to 7.6 (m, 6H); 7.7 (s, 1H); 7.9 (d, 2H); 8.1 (d, 2H); 8.3 (d, 1H); 8.4 (d, 1H); 15.0 (s, 1H). (Keto/enol mixture: 40/60).

2.2 2-(4-bromopyridin-2-yl)-1-(4-chlorophenyl)ethanone oxime 8.4 g (27.05 mmol) of 2-(4-bromopyridin-2-yl)-1-(4-chlorophenyl)ethanone are placed in 150 ml of ethanol in a round-bottomed flask. 22 ml (272.56 mmol) of pyridine and 7.5 g (107.93 mmol) of hydroxylamine monohydrochloride are added. The mixture is subsequently stirred at ambient temperature for 5 hours and then the reaction medium is concentrated under reduced pressure until a pasty yellow solid is obtained, which solid is taken up in 400 ml of ethyl acetate and 400 ml of water. The organic phase is separated and the aqueous phase is extracted three times with 200 ml of ethyl acetate. The organic phases are subsequently combined, dried over sodium sulphate and filtered. The filtrate is concentrated under reduced pressure: 8.1 g (91.9%) of compound are obtained in the form of a blue powder.

LC-MS: M+H=325
¹H NMR (d₆-DMSO) δ (ppm): 4.3 (s, 2H); 7.45 (m, 2H); 7.50 (d, 1H); 7.55 (s, 1H); 7.75 (m, 2H); 8.35 (d, 1H); 11.65 (s, 1H).

2.3. 5-bromo-2-(4-chlorophenyl)pyrazolo[1,5-a]pyridine 12.9 g (45.21 mmol) of ethyl O-(2-mesitylenesulphonyl)acetohydroxamate are placed in 30 ml of 1,4-dioxane in a round-bottomed flask. The mixture is cooled to 0° C. and 13.5 ml (156.60 mmol) of perchloric acid (70% in water) are added. 10 ml of 1,4-dioxane are subsequently added and then the medium is vigorously stirred at 0° C. for 2 h 30 minutes. The medium is subsequently poured into 350 ml of ice-cold water. The medium is left at approximately 0° C. for 10 minutes and then the white solid formed is recovered by filtration on a sintered glass funnel (do not completely dry, the product is potentially explosive in the dry state). The pasty white solid obtained is washed with 350 ml of ice-cold water and is then taken up in 250 ml of 1,2-dichloroethane and 150 ml of brine cooled to approximately 5° C. The organic phase is recovered and is filtered through a hydrophobic cartridge (70 ml liquid/liquid extraction column, Radleys®). The filtrate is recovered and is added dropwise to a solution, cooled to approximately 0° C., of 8.1 g (24.88 mmol) of 2-(4-bromopyridin-2-yl)-1-(4-chlorophenyl)ethanone oxime (compound obtained in stage 2.2) in 150 ml of 1,2-dichloroethane. After the addition, the mixture is allowed to return to ambient temperature and is stirred at ambient temperature for 3 hours. 250 ml of dichloromethane, 200 ml of water and 100 ml of an aqueous NaOH solution (1N) are subsequently added successively to the medium. The mixture is left stirring and is then separated by settling. The organic phase is separated and the aqueous phase is extracted with 2 times 200 ml of dichloromethane. The organic phases are subsequently combined, filtered through a hydrophobic cartridge (70 ml liquid/liquid extraction column, Radleys®) and then mixed with 15 g of silica. The filtrate is subsequently concentrated under reduced pressure: a brown powder is obtained, which powder is used as solid deposit for chromatography on silica gel, elution being carried out with a mixture of cyclohexane and dichloromethane (1/1). 5.8 g (75%) of compound are obtained in the form of a slightly yellow fluffy solid.

LC-MS: M+H=307
¹H NMR (d₆-DMSO) δ (ppm): 7.0 (d, 1H); 7.1 (s, 1H); 7.6 (d, 2H); 8.0 (s, 1H); 8.1 (d, 2H); 8.7 (d, 1H).

2.4. 2-(4-chlorophenyl)-5-(3-methoxymethylphenyl)pyrazolo[1,5-a]pyridine (Compound No. 9)

150 mg (0.49 mmol) of 5-bromo-2-(4-chlorophenyl)pyrazolo[1,5-a]pyridine, obtained according to the protocol described in Examples 1.3 or 2.3, 0.900 g (0.54 mmol) of 3-methoxymethylphenylboronic acid, 0.475 g (1.46 mmol) of caesium carbonate and 0.04 g (0.05 mmol) of [1,1'-bis(diphenylphosphino)ferrocene]dichloropalladium(II) are placed in a reactor containing 5 ml of a THF/water (9/1) mixture. The medium is brought to 70° C. for 2 hours and is then brought back to ambient temperature. The medium is subsequently diluted with 40 ml of dichloromethane and 40 ml of water. The medium is filtered through a hydrophobic cartridge (70 ml liquid/liquid extraction column, Radleys®) and 2 g of silica are added to the filtrate obtained. After concentrating under reduced pressure, the residue obtained is purified by chromatography on silica gel, elution being carried out with a mixture of cyclohexane and ethyl acetate (7/3). 0.14 g (82%) of the expected product is obtained in the form of a pale yellow powder.

Melting point (° C.): 130-132.
LC-MS: M+H=349
¹H NMR (d₆-DMSO) δ (ppm): 3.35 (s, 3H); 4.55 (s, 2H); 7.15 (s, 1H); 7.30 (d, 1H); 7.40 (s, 1H); 7.55 (m, 3H); 7.80 (m, 2H); 8.05 (m, 3H); 8.80 (d, 1H).

EXAMPLE 3

{4-[2-(4-chlorophenyl)pyrazolo[1,5-a]pyridin-5-yl]phenyl}methanol (Compound 10 of the Table)

300 mg (0.98 mmol) of 5-bromo-2-(4-chlorophenyl)pyrazolo[1,5-a]pyridine (compound obtained according to the protocol described in Examples 1.3 or 2.3), 180 mg (1.18 mmol) of 4-(hydroxymethyl)phenylboronic acid, 975 mg (2.99 mmol) of caesium carbonate and 85 mg (0.10 mmol) of [1,1'-bis(diphenylphosphino)ferrocene]dichloropalladium (II) are placed in a reactor tube containing 5 ml of a THF/water (9/1) mixture. The reaction mixture is heated at 60° C. for 2 hours and is then brought back to ambient temperature. The reaction medium is then diluted with 50 ml of water and 50 ml of dichloromethane and then filtered through a hydrophobic cartridge (70 ml liquid/liquid extraction column, Radleys®). 2 g of silica are added to the filtrate before concentrating it under reduced pressure. The brown powder obtained is used as solid deposit for chromatography on silica gel, elution being carried out with a mixture of cyclohexane and ethyl acetate (7/3). 262 mg (80%) of compound are obtained in the form of a grey powder.

Melting point (° C.): 214-216.
LC-MS: M+H=335
¹H NMR (d₆-DMSO) δ (ppm): 4.60 (d, 2H); 5.30 (d, 1H); 7.20 (s, 1H); 7.30 (d, 1H); 7.45 (d, 2H); 7.60 (d, 2H); 7.80 (d, 2H); 8.05 (m, 3H); 8.80 (d, 1H).

EXAMPLE 4

{2-[2-(4-chlorophenyl)pyrazolo[1,5-a]pyridin-5-yl]phenyl}methanol (Compound 11 of the Table)

The procedure described in Example 3 is followed. Starting from 0.3 g (0.98 mmol) of 5-bromo-2-(4-chlorophenyl)pyrazolo[1,5-a]pyridine, obtained according to the protocol described in Examples 1.3 or 2.3, 0.18 mg (1.18 mmol) of 2-(hydroxymethyl)phenylboronic acid, 0.975 g (2.99 mmol) of caesium carbonate, 0.085 g (0.10 mmol) of [1,1'-bis(diphenylphosphino)ferrocene]dichloropalladium(II) and 5 ml of a THF/water (9/1) mixture and after chromatographing on silica gel, elution being carried out with a mixture of cyclohexane and ethyl acetate (7/3), 0.303 g (92%) of the expected product is obtained in the form of a white powder.

Melting point (° C.): 144-146.

LC-MS: M+H=335

$^1$H NMR (d$_6$-DMSO) δ (ppm): 4.50 (d, 2H); 5.25 (d, 1H); 7.00 (d, 1H); 7.15 (s, 1H); from 7.40 to 7.50 (m, 3H); from 7.55 to 7.65 (m, 3H); 7.75 (s, 1H); 8.05 (d, 2H); 8.75 (d, 1H).

EXAMPLE 5

{3-[2-(4-fluorophenyl)pyrazolo[1,5-a]pyridin-5-yl]phenyl}methanol (Compound 6 of the Table)

5.1
2-(4-bromopyridin-2-yl)-1-(4-fluorophenyl)ethanone 5.0 g (29.07 mmol) of 4-bromo-2-picoline and 10.2 g (60.95 mmol) of ethyl 4-fluorobenzoate are placed under a stream of nitrogen in a round-bottomed flask and dissolved in 50 ml of anhydrous tetrahydrofuran. The solution is cooled to 0° C. and 70 ml (70 mmol) of a lithium hexamethyldisilazane solution (1M in tetrahydrofuran) are added dropwise. After addition, the mixture is stirred at ambient temperature for 2 h and cooled to 5° C., and then 100 ml of water are gradually added. The medium is subsequently diluted with 250 ml of ethyl acetate and 100 ml of water. The organic phase is separated and the aqueous phase is extracted twice with 100 ml of ethyl acetate. The organic phases are subsequently combined, dried over sodium sulphate and filtered. 15 g of silica are subsequently added to the filtrate and the mixture is stirred and then concentrated under reduced pressure. The powder obtained is used as solid deposit for chromatography on silica gel with a mixture of cyclohexane and ethyl acetate (9/1) as eluent. 7.5 g (88%) of compound are obtained in the form of a yellow powder.

LC-MS: M+H=294 (keto/enol ratio: 43/57)

$^1$H NMR (d$_6$-DMSO) δ (ppm): 4.56 (s, 2H); 6.34 (s, 1H); from 7.23 to 7.40 (m, 5H); 7.53 (d, 1H); 7.56 (m, 1H); 7.70 (d, 1H); from 7.81 to 7.92 (m, 2H); from 8.04 to 8.16 (m, 2H); 8.29 (d, 1H); 8.37 (d, 1H); 15.0 (s, 1H).

5.2 2-(4-bromopyridin-2-yl)-1-(4-fluorophenyl)ethanone oxime 7.5 g (24.26 mmol) of 2-(4-bromopyridin-2-yl)-1-(4-fluorophenyl)ethanone are placed in a round-bottomed flask containing 100 ml of absolute ethanol. 20 ml (247.78 mmol) of pyridine and 7.08 g (101.88 mmol) of hydroxylamine monohydrochloride are added before leaving the medium to stir at ambient temperature for 3 h. The ethanol is subsequently evaporated under vacuum and the residue obtained is taken up in 250 ml of water and 250 ml of ethyl acetate. The organic phase is separated and then the aqueous phase is extracted 5 times with 150 ml of ethyl acetate. The organic phases are subsequently combined, dried over sodium sulphate and concentrated under vacuum. 7.82 g of compound are obtained.

LC-MS: M+H=309

$^1$H NMR (d$_6$-DMSO, δ in ppm): 4.26 (s, 2H); 7.19 (t, 2H); 7.50 (m, 2H); 7.75 (m, 2H); 8.33 (d, 1H); 11.50 (s, 1H). ((E) oxime obtained).

5.3
5-bromo-2-(4-fluorophenyl)pyrazolo[1,5-a]pyridine 7.82 g (25.50 mmol) of 2-(4-bromopyridin-2-yl)-1-(4-fluorophenyl)ethanone oxime are placed in a round-bottomed flask and dissolved in 400 ml of 1,2-dichloroethane. A solution of O-(mesitylenesulphonyl)hydroxylamine (0.27M in 1,2-dichloroethane—compound obtained according to the protocol described in 1.3) is added dropwise to the medium, cooled to approximately 0° C. After the addition, the medium is stirred at ambient temperature for 1 h 30. The medium is subsequently diluted with 200 ml of water and 200 ml of a sodium hydroxide solution (1N). The two-phase medium is stirred and then separated by settling. The organic phase is separated and then the aqueous phase is extracted 4 times with 200 ml of dichloromethane. The organic phases are subsequently combined, dried over sodium sulphate and filtered. 15 g of silica are subsequently added to the filtrate and then the mixture is concentrated under reduced pressure. The powder obtained is used as solid deposit for chromatography on silica gel with a mixture of cyclohexane and dichloromethane (1/1) as eluent. 5.06 g (68%) of compound are obtained in the form of a white fluffy powder.

LC-MS: M+H=291

$^1$H NMR (d$_6$-DMSO, δ ppm): from 7.00 to 7.10 (m, 2H); 7.45 (m, 2H); 8.05 (m, 3H); 8.70 (d, 1H).

5.4 {3-[2-(4-fluorophenyl)pyrazolo[1,5-a]pyridin-5-yl]phenyl}methanol (Compound No. 6)

The procedure described in Example 3 is followed. Starting from 0.300 g (1.03 mmol) of 5-bromo-2-(4-fluorophenyl)pyrazolo[1,5-a]pyridine, obtained in stage 5.3, 0.190 g (1.25 mmol) of 3-(hydroxymethyl)phenylboronic acid, 1.00 g (3.07 mmol) of caesium carbonate, 0.085 g (0.10 mmol) of [1,1'-bis(diphenylphosphino)ferrocene]dichloropalladium(II) and 5 ml of a THF/water (9/1) mixture and after chromatographing on silica gel, elution being carried out with a mixture of cyclohexane and ethyl acetate (7/3), 0.245 g (74%) of the expected product is obtained in the fottn of a white powder.

Melting point (° C.): 141-143.

LC-MS: M+H=319

$^1$H NMR (d$_6$-DMSO) δ (ppm): 4.65 (d, 2H); 5.30 (t, 1H); 7.10 (s, 1H); from 7.25 to 7.40 (m, 4H); 7.50 (m, 1H); 7.70 (d, 1H); 7.80 (s, 1H); 8.00 (s, 1H); 8.05 (t, 2H); 8.80 (d, 1H).

EXAMPLE 6

1-{3-[2-(4-chlorophenyl)pyrazolo[1,5-a]pyridin-5-yl]phenyl}ethanol (Compound 3 of the Table)

6.1 3-[2-(4-chlorophenyl)pyrazolo[1,5-a]pyridin-5-yl]benzaldehyde 0.300 g (0.98 mmol) of 5-bromo-2-(4-chlorophenyl)pyrazolo[1,5-a]pyridine, obtained according to the protocol described in Examples 1.3 or 2.3, 0.292 g (1.95 mmol) of 3-formylphenylboronic acid and 0.94 g (2.88 mmol) of caesium carbonate are introduced into 5 ml of a 9/1 mixture of tetrahydrofuran and water under a stream of nitrogen. 0.08 g (0.10 mmol) of [1,1'-bis(diphenylphosphino)ferrocene]dichloropalladium(II) is added and the medium is heated at 70° C. for 2 hours. The medium is subsequently brought back to ambient temperature and then diluted with dichloromethane and water. The medium is filtered through a hydrophobic cartridge (70 ml liquid/liquid extraction column, Radleys®), and the organic phase is recovered, to which 2 g of silica are added. After evaporating the solvent, the residue is purified by chromatography on silica gel, elution being carried out with a mixture of cyclohexane and ethyl acetate (9/1). 0.302 g (93%) of the expected product is obtained in the form of a yellow powder.

Melting point (° C.): 152-154
LC-MS: M+H=333
$^1$H NMR (d$_6$-DMSO) δ (ppm): 7.2 (s, 1H); 7.35 (d, 1H); 7.55 (d, 2H); 7.75 (t, 1H); 7.95 (d, 1H); 8.05 (d, 2H); 8.15 (s, 1H); 8.20 (d, 1H); 8.40 (s, 1H); 8.85 (d, 1H); 10.15 (s, 1H).

6.2 1-{3-[2-(4-chlorophenyl)pyrazolo[1,5-a]pyridin-5-yl]phenyl}ethanol (Compound 3 of the Table)

0.085 g (0.26 mmol) of 3-[2-(4-chlorophenyl)pyrazolo[1,5-a]pyridin-5-yl]benzaldehyde is dissolved in 8 ml of tetrahydrofuran under a stream of nitrogen. The medium is cooled to 5° C. before slow addition of 0.30 ml (0.90 mmol) of a methylmagnesium bromide solution (3M in ethyl ether). The medium is subsequently stirred at ambient temperature for 2 hours. Neutralization is carried out by adding, under cold conditions and dropwise, a saturated aqueous ammonium chloride solution and then dilution is carried out with ethyl acetate and water. The organic phase is separated and then the aqueous phase is extracted twice with ethyl acetate. The organic phases are combined, dried over sodium sulphate, filtered and concentrated under vacuum. The residue is purified by chromatography on silica gel (by solid deposit), elution being carried out with a mixture of cyclohexane and ethyl acetate (8/2). 0.048 g (53%) of the expected product is obtained in the form of a white powder.

Melting point (° C.): 93-95.
LC-MS: M+H=349
$^1$H NMR (d$_6$-DMSO) δ (ppm): 1.45 (d, 3H); 4.85 (m, 1H); 5.25 (d, 1H); 7.15 (s, 1H); 7.30 (d, 1H); 7.45 (m, 2H); 7.60 (m, 2H); 7.70 (d, 1H); 7.80 (s, 1H); 8.05 (m, 3H); 8.80 (d, 1H).

EXAMPLE 7

1-{3-[2-(4-chlorophenyl)pyrazolo[1,5-a]pyridin-5-yl]phenyl}cyclopropylmethanol (Compound 4 of the Table)

The procedure described in stage 6.2 is followed. Starting from 0.15 g (0.45 mmol) of 3-[2-(4-chlorophenyl)pyrazolo[1,5-a]pyridin-5-yl]benzaldehyde, obtained according to the process described in 6.1, in solution in 8 ml of tetrahydrofuran, followed by addition of 1.80 ml (0.9 mmol) of a cyclopropylmagnesium bromide solution (0.5M in tetrahydrofuran) and after chromatographing on silica gel, elution being carried out with a mixture of cyclohexane and ethyl acetate (8/2), 0.1 g (59%) of the expected product is obtained in the form of a beige powder.

Melting point (° C.): 141-143.
LC-MS: M+H=375
$^1$H NMR (d$_6$-DMSO) δ (ppm): 0.45 (m, 4H); 1.15 (m, 1H); 4.10 (m, 1H); 5.25 (s, 1H); 7.15 (s, 1H); 7.30 (d, 1H); 7.50 (m, 2H); 7.60 (d, 2H); 7.70 (m, 1H); 7.80 (s, 1H); 8.00 (s, 1H); 8.10 (d, 2H); 8.80 (d, 1H).

EXAMPLE 8

1-{3-[2-(4-fluorophenyl)pyrazolo[1,5-a]pyridin-5-yl]phenyl}ethanol (Compound 8 of the Table)

8.1 3-[2-(4-fluorophenyl)pyrazolo[1,5-a]pyridin-5-yl]benzaldehyde 0.200 g (0.69 mmol) of 5-bromo-2-(4-fluorophenyl)pyrazolo[1,5-a]pyridine, obtained in stage 5.3, 0.125 g (0.83 mmol) of 3-formylphenylboronic acid and 0.670 g (2.06 mmol) of caesium carbonate are introduced under a stream of nitrogen into 5 ml of a 9/1 mixture of tetrahydrofuran and water. 0.055 g (0.07 mmol) of [1,1'-bis(diphenylphosphino)ferrocene]-dichloropalladium(II) is added and the medium is heated at 70° C. for 3 hours. A further 0.063 g (0.42 mmol) of 3-formylphenylboronic acid, 0.335 g (1.03 mmol) of caesium carbonate and 0.028 g (0.03 mmol) of [1,1'-bis(diphenylphosphino)ferrocene]dichloro-palladium(II) are subsequently added while leaving to stir at 70° C. for 4 h. The medium is subsequently brought back to ambient temperature and then diluted with dichloromethane and water. The two-phase medium is filtered through a hydrophobic cartridge (70 ml liquid/liquid extraction column, Radleys®) and the organic phase is recovered, to which 1.2 g of silica are added. After evaporating the solvent, the residue is purified by chromatography on silica gel, elution being carried out with a mixture of cyclohexane and ethyl acetate (8/2). 0.175 g (80%) of the expected product is obtained in the form of a white powder.

LC-MS: M+H=317
$^1$H NMR (d$_6$-DMSO) δ (ppm): 7.15 (s, 1H); from 7.30 to 7.37 (m, 3H); 7.77 (t, 1H); 7.98 (m, 1H); 8.08 (m, 2H); 8.15 (m, 1H); 8.20 (m, 1H); 8.38 (s, 1H); 8.82 (d, 1H); 10.15 (s, 1H).

8.2 1-{3-[2-(4-fluorophenyl)pyrazolo[1,5-a]pyridin-5-yl]phenyl}ethanol (Compound 8 of the Table)

0.072 g (0.23 mmol) of 3-[2-(4-fluorophenyl)pyrazolo[1,5-a]pyridin-5-yl]benzaldehyde are dissolved in 10 ml of tetrahydrofuran under a stream of nitrogen. The medium is cooled to 0° C. for slow addition of 0.23 ml (0.68 mmol) of a methylmagnesium bromide solution (3M in ethyl ether). The medium is subsequently brought back to ambient temperature and stirred for 1 hour 30 minutes. Neutralization is carried out by adding, under cold conditions and dropwise, a saturated aqueous ammonium chloride solution and then dilution is carried out with dichloromethane and water. The pH of the medium is adjusted to 9-10 by addition of a saturated aqueous sodium carbonate solution. The medium is filtered through a hydrophobic cartridge (70 ml liquid/liquid extraction column, Radleys®) and the organic phase is recovered and concentrated under reduced pressure after having added 0.8 g of silica. The residue obtained is purified by chromatography on silica gel, elution of the solid deposit being carried out with a mixture of cyclohexane and ethyl acetate (8/2). 0.056 g (74%) of the expected product is obtained in the form of a white powder.

Melting point (° C.): 132-134.
LC-MS: M+H=333
$^1$H NMR (d$_6$-DMSO, δ in ppm): 1.42 (d, 3H); 4.85 (q, 1H); 5.25 (s, 1H); 7.11 (s, 1H); 7.25 (d, 1H); 7.34 (m, 2H); from 7.40 to 7.50 (m, 2H); 7.69 (d, 1H); 7.80 (d, 1H); 8.00 (s, 1H); 8.08 (m, 2H); 8.75 (d, 1H).

EXAMPLE 9

2-{3-[2-(4-chlorophenyl)pyrazolo[1,5-a]pyridin-5-yl]phenyl}propan-2-ol (Compound 2 of the Table)

9.1 methyl 3-[2-(4-chlorophenyl)pyrazolo[1,5-a]pyridin-5-yl]benzoate

The procedure described in Example 3 is followed. Starting from 1.5 g (4.88 mmol) of 5-bromo-2-(4-chlorophenyl)pyrazolo[1,5-a]pyridine, obtained according to the protocol described in Examples 1.3 or 2.3, 1.05 mg (5.83 mmol) of 3-methoxycarbonylphenylboronic acid, 4.6 g (14.61 mmol) of caesium carbonate, 0.400 g (0.49 mmol) of [1,1'-bis(diphenyl-phosphino)ferrocene]dichloropalladium(II) and 20 ml of a THF/water (9/1) mixture and after chromatographing on silica gel, elution being carried out with a mixture of cyclohexane and ethyl acetate (9/1), 1.6 g (90%) of the expected product are obtained in the form of a yellow-white powder.

Melting point (° C.): 180-182
LC-MS: M+H=363
$^1$H NMR (d$_6$-DMSO) δ (ppm): 3.95 (s, 3H); 7.20 (s, 1H); 7.35 (d, 1H); 7.60 (d, 2H); 7.70 (t, 1H); from 8.00 to 8.20 (m, 5H); 8.35 (s, 1H); 8.85 (d, 1H).

9.2 2-{3-[2-(4-chlorophenyl)pyrazolo[1,5-a]pyridin-5-yl]phenyl}propan-2-ol (Compound No. 2)

0.13 g (0.36 mmol) of methyl 3-[2-(4-chlorophenyl)pyrazolo[1,5-a]pyridin-5-yl]benzoate is dissolved in 8 ml of tetrahydrofuran under a stream of nitrogen. The medium is cooled to 0° C. for slow addition of 0.6 ml (1.80 mmol) of a methylmagnesium bromide solution (3M in ethyl ether). The medium is subsequently brought back to ambient temperature and stirred for 2 hours. Neutralization is carried out by adding, under cold conditions and dropwise, a saturated aqueous ammonium chloride solution and then the medium is diluted with 50 ml of dichloromethane and 50 ml of water. The medium is filtered through a hydrophobic cartridge (70 ml liquid/liquid extraction column, Radleys®) and the organic phase is recovered and concentrated under reduced pressure after having added 0.4 g of silica. The residue is purified by chromatography on silica gel, the solid deposit being eluted with a mixture of cyclohexane and ethyl acetate (8/2). 0.08 g (61%) of the expected product is obtained in the form of a white powder.

Melting point (° C.): 159-161.
LC-MS: M+H=363
$^1$H NMR (d$_6$-DMSO) δ (ppm): 1.50 (s, 6H); 5.10 (s, 1H); 7.15 (s, 1H); 7.30 (d, 2H); 7.45 (t, 1H); 7.55 (m, 2H); 7.70 (m, 1H); 7.90 (s, 1H); 8.00 (m, 1H); 8.05 (m, 2H); 8.80 (d, 1H).

EXAMPLE 10

2-{3-[2-(4-fluorophenyl)pyrazolo[1,5-a]pyridin-5-yl]phenyl}propan-2-ol (Compound 7 of the Table)

10.1 methyl 3-[2-(4-fluorophenyl)pyrazolo[1,5-a]pyridin-5-yl]benzoate 0.400 g (1.37 mmol) of 5-bromo-2-(4-fluorophenyl)pyrazolo[1,5-a]pyridine, obtained in stage 5.3, 0.300 g (1.67 mmol) of 3-methoxycarbonylphenylboronic acid and 1.330 g (4.08 mmol) of caesium carbonate are introduced under a stream of nitrogen into 5 ml of a 9/1 mixture of tetrahydrofuran and water. 0.11 g (0.13 mmol) of [1,1'-bis(diphenylphosphino)ferrocene]dichloropalladium(II) is added and the medium is heated at 70° C. for 4 hours. The medium is subsequently brought back to ambient temperature and then diluted with 40 ml of dichloromethane and 40 ml of water. The medium is subsequently filtered through a hydrophobic cartridge (70 ml liquid/liquid extraction column, Radleys®) and the organic phase is recovered and concentrated under reduced pressure after having added 2 g of silica. The residue is purified by chromatography on silica gel, elution being carried out with a mixture of cyclohexane and ethyl acetate (9/1). 0.340 g (71%) of the expected product is obtained in the form of a white powder.

LC-MS: M+H=347
$^1$H NMR (d$_6$-DMSO) δ (ppm): 3.95 (s, 3H); 7.15 (s, 1H); from 7.30 to 7.40 (m, 3H); 7.70 (t, 1H); from 8.00 to 8.15 (m, 5H); 8.35 (s, 1H); 8.80 (d, 1H).

10.2 2-{3-[2-(4-fluorophenyl)pyrazolo[1,5-a]pyridin-5-yl]phenyl}propan-2-ol (Compound No. 7)

0.200 g (0.58 mmol) of methyl 3-[2-(4-fluorophenyl)pyrazolo[1,5-a]pyridin-5-yl]benzoate is dissolved in 15 ml of tetrahydrofuran under a stream of nitrogen. The medium is cooled to 5° C. for slow addition of 1 ml (3.00 mmol) of a methylmagnesium bromide solution (3M in ethyl ether). The medium is subsequently brought back to ambient temperature and stirred for 2 hours. Neutralization is carried out by adding, under cold conditions and dropwise, 10 ml of a saturated aqueous ammonium chloride solution and then dilution is carried out with 100 ml of dichloromethane and 100 ml of water. The aqueous phase is extracted with two times 50 ml of dichloromethane. The organic phases are combined, filtered through a hydrophobic cartridge (70 ml liquid/liquid extraction column, Radleys®) and concentrated under vacuum after having added 2 g of silica. The residue is purified by chromatography on silica gel, elution of the solid deposit being carried out with a mixture of cyclohexane and ethyl acetate (7/3). 0.165 g (82%) of the expected product is obtained in the form of a white powder.

Melting point (° C.): 162-164.
LC-MS: M+H=347
$^1$H NMR (d$_6$-DMSO) δ (ppm): 1.50 (s, 6H); 5.10 (s, 1H); 7.10 (s, 1H); 7.25 (d, 1H); 7.35 (t, 2H); 7.45 (t, 1H); 7.55 (m, 1H); 7.65 (m, 1H); 7.90 (s, 1H); 8.00 (s, 1H); 8.10 (t, 2H); 8.80 (d, 1H).

EXAMPLE 11

{3-[2-(4-chlorophenyl)pyrazolo[1,5-a]pyridin-5-yl]-2,6-difluorophenyl}-methanol (Compound 5 of the Table)

11.1 3-[2-(4-chlorophenyl)pyrazolo[1,5-a]pyridin-5-yl]-2,6-difluorobenzaldehyde 0.200 g (0.65 mmol) of 5-bromo-2-(4-chlorophenyl)pyrazolo[1,5-a]pyridine, obtained according to the protocol described in Examples 1.3 or 2.3, 0.145 g (0.78 mmol) of 2,4-difluoro-3-formylphenylboronic acid and 0.640 g (1.96 mmol) of caesium carbonate are introduced under a stream of nitrogen into 5 ml of a 9/1 mixture of tetrahydrofuran and water. 0.055 g (0.07 mmol) of [1,1'-bis(diphenylphosphino)ferrocene]dichloropalladium(II) is added and the medium is heated at 60° C. for 2 hours. The medium is subsequently brought back to ambient temperature and then diluted with 50 ml of dichloromethane and 50 ml of water. The organic phase is recovered and filtered through a hydrophobic cartridge (70 ml liquid/liquid extraction column, Radleys®). 1.8 g of silica are added to the filtrate recovered and then the mixture is concentrated under reduced pressure. The powder obtained is purified by chromatography on silica gel, elution being carried out with a mixture of cyclohexane and ethyl acetate (8/2). 0.195 g (81%) of the expected product is obtained in the form of a white powder.

Melting point (° C.): 187-189
LC-MS: M+H=369
$^1$H NMR (d$_6$-DMSO) δ (ppm): 7.15 (d, 1H); 7.25 (s, 1H); 7.45 (t, 1H); 7.60 (d, 2H); 7.95 (s, 1H); 8.10 (m, 3H); 8.85 (d, 1H); 10.35 (s, 1H).

11.2 {3-[2-(4-chlorophenyl)pyrazolo[1,5-a]pyridin-5-yl]-2,6-difluorophenyl}-methanol (Compound No. 5)

0.040 g (1.06 mmol) of sodium borohydride is added portionwise to a solution, cooled to approximately 5° C., of 0.135 g (0.37 mmol) of 3-[2-(4-chlorophenyl)pyrazolo[1,5-a]pyridin-5-yl]-2,6-difluorobenzaldehyde in 10 ml of a mixture of methanol and tetrahydrofuran (1/1). The medium is stirred at ambient temperature for 1 hour, then cooled to 5° C. and then hydrolysed by dropwise addition of 10 ml of a saturated aqueous ammonium chloride solution and 10 ml of water. The mixture is concentrated under reduced pressure and the residue obtained is taken up in 50 ml of dichloromethane and 50 ml of water. The medium is subsequently filtered through a hydrophobic cartridge (70 ml liquid/liquid extraction column, Radleys®) and the organic phase is recovered and concentrated under reduced pressure after having added 1 g of silica. The residue is purified by chromatography on silica gel, elution being carried out with a mixture of cyclohexane and ethyl acetate (8/2). 0.065 g (48%) of the expected product is obtained in the form of a white powder.

Melting point (° C.): 190-192.
LC-MS: M+H=371
$^1$H NMR (d$_6$-DMSO) δ (ppm): 4.60 (d, 2H); 5.35 (t, 1H); 7.10 (d, 1H); 7.20 (s, 1H); 7.25 (t, 1H); 7.60 (d, 2H); 7.70 (m, 1H); 7.90 (s, 1H); 8.05 (d, 2H); 8.80 (d, 1H).

EXAMPLE 12

6-[2-(4-chlorophenyl)pyrazolo[1,5-a]pyridin-5-yl]indan-1-ol (Compound 12 of the Table)

12.1 2-(4-chlorophenyl)-5-(4,4,5,5-tetramethyl-1,3,2-dioxaborolan-2-yl)pyrazolo-[1,5-a]pyridine 1.75 g (5.69 mmol) of 5-bromo-2-(4-chlorophenyl)pyrazolo[1,5-a]pyridine, 1.73 g (6.82 mmol) of bis(pinacolato)diboron and 1.67 g (17.03 mmol) of potassium acetate are placed in 15 ml of 1,4-dioxane in two microwave reactors. 930 mg (0.57 mmol) of [1,1'-bis(diphenylphosphino)ferrocene]dichloropalladium(II) are then added and the 2 media are each irradiated at 140° C. for 20 minutes.

The 2 reaction media are then mixed and then diluted with 300 ml of dichloromethane and 200 ml of water. The organic phase is separated and the aqueous phase is extracted with 3 times 200 ml of dichloromethane. The organic phases are subsequently combined and then 10 g of silica are added to the solution obtained before concentrating it under reduced pressure: production of a black powder which is used as solid deposit for chromatography on silica gel, elution being carried out with a mixture of cyclohexane and ethyl acetate (9/1). 3.0 g (74%) of compound are obtained in the form of an orangey solid.

LC-MS: M+H=355 (decomposition of the product, formation of boronic acid M+H=273)
$^1$H NMR (d$_6$-DMSO) δ (ppm): 1.35 (s, 12H); 7.0 (d, 1H); 7.22 (s, 1H); 7.55 (m, 2H); 8.0 (m, 3H); 8.1 (d, 2H); 8.7 (d, 1H).

12.2 6-[2-(4-chlorophenyl)pyrazolo[1,5-a]pyridin-5-yl]indanone

The procedure described in Example 3 is followed. Starting from 0.2 g (0.56 mmol) of 2-(4-chlorophenyl)-5-(4,4,5,5-tetramethyl-1,3,2-dioxaborolan-2-yl)pyrazolo[1,5-a]pyridine, obtained in stage 12.1, 0.24 mg (1.14 mmol) of 6-bromo-1-indanone, 0.55 g (1.69 mmol) of caesium carbonate, 0.046 g (0.06 mmol) of [1,1'-bis(diphenylphosphino)ferrocene]dichloro-palladium(II) and 5 ml of a THF/water (9/1) mixture and after chromatographing on silica gel, elution being carried out with a mixture of cyclohexane and ethyl acetate (8/2), 0.127 g (62%) of the expected product is obtained in the form of a yellow powder.

LC-MS: M+H=359
$^1$H NMR (d$_6$-DMSO) δ (ppm): 2.72 (m, 2H); 3.20 (m, 2H); 7.15 (s, 1H); 7.35 (dd, 1H); 7.55 (m, 2H); 7.75 (m, 1H); from 8.05 to 8.20 (m, 5H); 8.80 (d, 1H).

12.3 6-[2-(4-chlorophenyl)pyrazolo[1,5-a]pyridin-5-yl]indan-1-ol (Compound No. 12)

0.040 g (1.06 mmol) of sodium borohydride is added portionwise to a solution, cooled to approximately 5° C., of 0.12 g (0.33 mmol) of 6-[2-(4-chlorophenyl)pyrazolo[1,5-a]pyridin-5-yl]indanone in 16 ml of a 1/1 mixture of methanol and tetrahydrofuran. The medium is stirred at 70° C. for 2 hours, then cooled to 0° C. and then hydrolysed by dropwise addition of 10 ml of a saturated aqueous ammonium chloride solution. The medium is subsequently diluted with 50 ml of ethyl acetate and 30 ml of water. The organic phase is recovered and the aqueous phase is extracted with 30 ml of ethyl acetate. The organic phases are combined, dried over sodium sulphate and then concentrated under reduced pressure. The residue obtained by solid deposition is purified by chromatography on silica gel, elution being carried out with a mixture of cyclohexane and ethyl acetate (8/2). 0.080 g (66%) of the expected product is obtained in the form of a white powder.

Melting point (° C.): 181-183.
LC-MS: M+H=361
$^1$H NMR (d$_6$-DMSO) δ (ppm): 1.9 (m, 1H); 2.45 (m, 1H); 2.80 (m, 1H); 3.00 (m, 1H); 5.15 (m, 1H); 5.30 (d, 1H); 7.10 (s, 1H); 7.20 (d, 1H); 7.35 (d, 1H); 7.55 (d, 2H); 7.65 (d, 1H); 7.75 (s, 1H); 7.95 (s, 1H); 8.05 (m, 2H); 8.80 (d, 1H).

The tables which follow illustrate the chemical structures of general formula (I) (Table 1) and the physicochemical characteristics (Table 2) of a few examples of compounds according to the invention.

In these tables:
the "Position" column gives the position of substitution of the

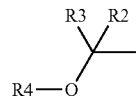

group on the phenyl nucleus (2, 3 or 4);
Ph means Phenyl;
the "M.p." column gives the melting points of the products in degrees Celsius (° C.).

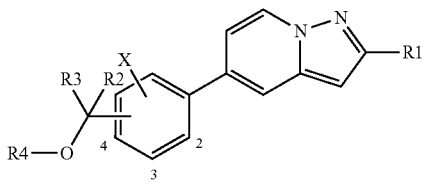

TABLE 1

| No. | R1 | Position | R2 | R4 | R3 | X |
|---|---|---|---|---|---|---|
| 1 | 4-Cl—Ph | 3 | H | H | H | H |
| 2 | 4-Cl—Ph | 3 | CH$_3$ | H | CH$_3$ | H |
| 3 | 4-Cl—Ph | 3 | CH$_3$ | H | H | H |
| 4 | 4-Cl—Ph | 3 | cyclopropyl | H | H | H |
| 5 | 4-Cl—Ph | 3 | H | H | H | 2,4-(F)$_2$ |
| 6 | 4-F—Ph | 3 | H | H | H | H |
| 7 | 4-F—Ph | 3 | CH$_3$ | H | CH$_3$ | H |
| 8 | 4-F—Ph | 3 | CH$_3$ | H | H | H |
| 9 | 4-Cl—Ph | 3 | H | CH$_3$ | H | H |
| 10 | 4-Cl—Ph | 4 | H | H | H | H |
| 11 | 4-Cl—Ph | 2 | H | H | H | H |
| 12 | 4-Cl—Ph | 3 | H | H | —(CH$_2$)$_2$—* | |

* For compound 12, X is in the 4 position.

TABLE 2

| No. | M.p. | NMR/[M + H] |
|---|---|---|
| 1 | 161-164° C. | $^1$H NMR (d$_6$-DMSO, δ in ppm): 4.6 (d, 2H); 5.3 (t, 1H); 7.1 (s, 1H); 7.3 (d, 1H); 7.4 (d, 1H); 7.5 (t, 1H); 7.6 (d, 2H); 7.7 (d, 1H); 7.8 (s, 1H); 8.0 (s, 1H); 8.1 (d, 2H); 8.8 (d, 1H); M + H = 335. |
| 2 | 159-161° C. | $^1$H NMR (d$_6$-DMSO) δ (ppm): 1.50 (s, 6H); 5.10 (s, 1H); 7.15 (s, 1H); 7.30 (d, 2H); 7.45 (t, 1H); 7.55 (m, 2H); 7.70 (m, 1H); 7.90 (s, 1H); 8.00 (m, 1H); 8.05 (m, 2H); 8.80 (d, 1H); M + H = 363 |
| 3 | 93-95° C. | $^1$H NMR (d$_6$-DMSO) δ (ppm): 1.45 (d, 3H); 4.85 (m, 1H); 5.25 (d, 1H); 7.15 (s, 1H); 7.30 (d, 1H); 7.45 (m, 2H); 7.60 (m, 2H); 7.70 (d, 1H); 7.80 (s, 1H); 8.05 (m, 3H); 8.80 (d, 1H); M + H = 349 |
| 4 | 141-143° C. | $^1$H NMR (d$_6$-DMSO) δ (ppm): 0.45 (m, 4H); 1.15 (m, 1H); 4.10 (m, 1H); 5.25 (s, 1H); 7.15 (s, 1H); 7.30 (d, 1H); 7.50 (m, 2H); 7.60 (d, 2H); 7.70 (m, 1H); 7.80 (s, 1H); 8.00 (s, 1H); 8.10 (d, 2H); 8.80 (d, 1H); M + H = 375 |
| 5 | 190-192° C. | $^1$H NMR (d$_6$-DMSO) δ (ppm): 4.60 (d, 2H); 5.35 (t, 1H); 7.10 (d, 1H); 7.20 (s, 1H); 7.25 (t, 1H); 7.60 (d, 2H); 7.70 (m, 1H); 7.90 (s, 1H); 8.05 (d, 2H); 8.80 (d, 1H); M + H = 371 |
| 6 | 141-143° C. | $^1$H NMR (d$_6$-DMSO) δ (ppm): 4.65 (d, 2H); 5.30 (t, 1H); 7.10 (s, 1H); from 7.25 to 7.40 (m, 4H); 7.50 (m, 1H); 7.70 (d, 1H); 7.80 (s, 1H); 8.00 (s, 1H); 8.05 (t, 2H); 8.80 (d, 1H); M + H = 319 |
| 7 | 162-164° C. | $^1$H NMR (d$_6$-DMSO) δ (ppm): 1.50 (s, 6H); 5.10 (s, 1H); 7.10 (s, 1H); 7.25 (d, 1H); 7.35 (t, 2H); 7.45 (t, 1H); 7.55 (m, 1H); 7.65 (m, 1H); 7.90 (s, 1H); 8.00 (s, 1H); 8.10 (t, 2H); 8.80 (d, 1H); M + H = 347 |
| 8 | 132-134° C. | $^1$H NMR (d$_6$-DMSO) δ (ppm): 1.42 (d, 3H); 4.85 (q, 1H); 5.25 (s, 1H); 7.11 (s, 1H); 7.25 (d, 1H); 7.34 (m, 2H); from 7.40 to 7.50 (m, 2H); 7.69 (d, 1H); 7.80 (d, 1H); 8.00 (s, 1H); 8.08 (m, 2H); 8.75 (d, 1H); M + H = 333. |
| 9 | 130-132° C. | $^1$H NMR (d$_6$-DMSO) δ (ppm): 3.35 (s, 3H); 4.55 (s, 2H); 7.15 (s, 1H); 7.30 (d, 1H); 7.40 (s, 1H); 7.55 (m, 3H); 7.80 (m, 2H); 8.05 (m, 3H); 8.80 (d, 1H); M + H = 349 |
| 10 | 214-216° C. | $^1$H NMR (d$_6$-DMSO) δ (ppm): 4.60 (d, 2H); 5.30 (d, 1H); 7.20 (s, 1H); 7.30 (d, 1H); 7.45 (d, 2H); 7.60 (d, 2H); 7.80 (d, 2H); 8.05 (m, 3H); 8.80 (d, 1H); M + H = 335 |
| 11 | 144-146° C. | $^1$H NMR (d$_6$-DMSO) δ (ppm): 4.50 (d, 2H); 5.25 (d, 1H); 7.00 (d, 1H); 7.15 (s, 1H); from 7.40 to 7.50 (m, 3H); from 7.55 to 7.65 (m, 3H); 7.75 (s, 1H); 8.05 (d, 2H); 8.75 (d, 1H); M + H = 335 |
| 12 | 181-183° C. | $^1$H NMR (d$_6$-DMSO) δ (ppm): 1.9 (m, 1H); 2.45 (m, 1H); 2.80 (m, 1H); 3.00 (m, 1H); 5.15 (m, 1H); 5.30 (d, 1H); 7.10 (s, 1H); 7.20 (d, 1H); 7.35 (d, 1H); 7.55 (d, 2H); 7.65 (d, 1H); 7.75 (s, 1H); 7.95 (s, 1H); 8.05 (m, 2H); 8.80 (d, 1H); M + H = 361 |

The compounds according to the invention have formed the subject of pharmacological assays which make it possible to determine their modulatory effect on NOT.

Evaluation of the In Vitro Activity on N2A Cells

The activity of the compounds according to the invention was evaluated on a cell line (N2A) endogenously expressing the mouse Nurr1 receptor and stably transfected with the NOT binding response element (NBRE) coupled to the luciferase reporter gene. The assays were carried out according to the procedure described below.

The Neuro-2A cell line comes from a standard commercial source (ATCC). The Neuro-2A clone was obtained, from a spontaneous tumour originating from an A albino mouse strain, by R. J Klebe et al. This Neuro-2A line is subsequently stably transfected with 8NBRE-luciferase. The N2A-8NBRE cells are cultured until confluence in 75 cm$^2$ culture flasks containing DMEM supplemented with 10% of foetal calf serum, 4.5 g/l of glucose and 0.4 mg/ml of geneticin. After a week of culture, the cells are recovered with 0.25% trypsin for 30 seconds and then resuspended in DMEM without phenol red, containing 4.5 g/l of glucose and 10% of Hyclone delipidized serum, and deposited into transparent-bottom 96-well white plates. The cells are deposited at a rate of 60 000 per well in 75 μl for 24 hours before the addition of the products. The products are applied in 25 μl and incubated for a further 24 hours. On the day of the measurement, an equivalent volume (100 μl) of Steadylite is added to each well and then left for a period of 30 minutes in order to obtain complete cell lysis and maximum signal production. The plates are subsequently measured in a luminescence counter for microplates after having been sealed with an adhesive film. The products are prepared in the form of a stock solution at $10^{-2}$M and then diluted in 100% of DMSO. Each product concentration is prediluted in culture medium before incubation with the cells, thus containing 0.625% final concentration of DMSO.

The best compounds have an EC$_{50}$ of between 0.1 nM and 10 μM.

For example, compounds Nos. 1, 11 and 12 showed an EC$_{50}$ value of 0.2, 1.7 and 164 nM respectively.

It is thus apparent that the compounds according to the invention have a modulatory effect on NOT.

The compounds of the present invention also have all the properties required for the development of a medicament, in particular an improved safety profile and activity profile.

The compounds according to the invention can thus be used in the preparation of medicaments for their therapeutic application in the treatment or prevention of diseases involving NOT receptors.

Thus, according to another of its aspects, a subject-matter of the invention is medicaments which comprise a compound of formula (I) or an addition salt of the latter with a pharmaceutically acceptable acid.

These medicaments are employed therapeutically, in particular in the treatment and prevention of neurodegenerative diseases, such as, for example, Parkinson's disease, Alzheimer's disease or tauopathies (for example, progressive supranuclear palsy, frontotemporal dementia, corticobasal degeneration or Pick's disease); cerebral traumas, such as ischaemia and cranial traumas and epilepsy; psychiatric diseases, such as schizophrenia, depression, substance dependence or attention deficit hyperactivity disorders; inflammatory diseases of the central nervous system, such as multiple sclerosis, encephalitis, myelitis and encephalomyelitis, and other inflammatory diseases, such as vascular pathologies, atherosclerosis, inflammations of the joints, arthrosis or rheumatoid arthritis; osteoarthritis, Crohn's disease, ulcerative colitis; allergic inflammatory diseases, such as asthma; autoimmune diseases, such as type 1 diabetes, lupus, scleroderma, Guillain-Barré syndrome, Addison's disease and other immune-mediated diseases; osteoporosis; or cancers.

These compounds might also be used as treatment associated with stem cell transplants and/or grafts.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt of the said compound, and also at least one pharmaceutically acceptable excipient.

The said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, can be administered in unit administration form, as a mixture with conventional pharmaceutical excipients, to animals and human beings for the prophylaxis or treatment of the above disorders or diseases.

The appropriate unit administration forms comprise oral fauns, such as tablets, soft or hard gelatin capsules, powders, granules and oral solutions or suspensions, forms for sublingual, buccal, intratracheal, intraocular or intranasal administration or for administration by inhalation, forms for topical, transdermal, subcutaneous, intramuscular or intravenous administration, forms for rectal administration and implants. For topical application, the compounds according to the invention can be used in creams, gels, ointments or lotions.

By way of example, a unit administration form of a compound according to the invention in the tablet form can comprise the following components:

| | |
|---|---:|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

There may be specific cases where higher or lower dosages are appropriate; such dosages do not depart from the scope of the invention. According to the usual practice, the dosage appropriate to each patient is determined by the physician according to the method of administration and the weight and the response of the said patient.

The present invention, according to another of its aspects, also relates to a method for the treatment of the pathologies indicated above which comprises the administration, to a patient, of an effective dose of a compound according to the invention or one of its pharmaceutically acceptable salts.

The invention claimed is:

1. A compound of formula (I):

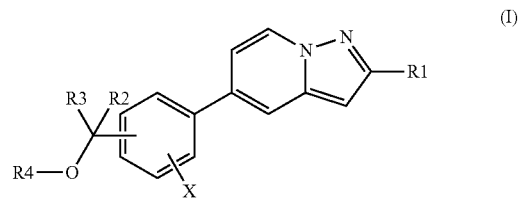

in which:
R1 represents:
   a phenyl group or a naphthyl group, it being possible for these two groups optionally to be substituted by one or more atoms or groups chosen, independently of one another, from the following atoms or groups: halogen, $(C_1-C_6)$alkyl, halo$(C_1-C_6)$alkyl, $(C_1-C_6)$alkoxy, halo$(C_1-C_6)$alkoxy, $(C_1-C_6)$thioalkyl, —S(O)$(C_1-C_6)$alkyl, —S(O)$_2$$(C_1-C_6)$alkyl, hydroxyl, hydroxy$(C_1-C_6)$alkylene, CHO, COOH, $(C_1-C_6)$alkoxy$(C_1-C_6)$alkyleneoxy, NRaRb, CONRaRb, SO$_2$NRaRb, NRcCORd, OC(O)NRaRb, OCO$(C_1-C_6)$alkyl, NRc-C(O)ORe or NRcSO$_2$Re,
X represents from 1 to 4 substituents which are identical to or different from one another and which are chosen from hydrogen, halogen, $(C_1-C_6)$alkyl or $(C_1-C_6)$alkoxy, it being possible for the $(C_1-C_6)$alkyl group to be optionally substituted by one or more atoms or groups chosen from a halogen, $(C_1-C_6)$alkoxy or hydroxyl;
R2 and R3 represent, independently of one another,
   a hydrogen atom,
   a $(C_1-C_6)$alkyl group optionally substituted by an Rf group;
   a CHO or COOH group,
X and R3 can together form, with the carbon atoms which carry them, a carbocycle of 5 to 7 carbon atoms;
R4 represents a hydrogen atom or a $(C_1-C_6)$alkyl group,
Ra and Rb represent, independently of one another, a hydrogen atom or a $(C_1-C_6)$alkyl, aryl$(C_1-C_6)$alkylene or aryl group;
or Ra and Rb together form, with the nitrogen atom which carries them, an azetidine, pyrrolidine, piperidine, azepine, morpholine, thiomorpholine, piperazine or homopiperazine group, this group being optionally substituted by a $(C_1-C_6)$alkyl, aryl or aryl$(C_1-C_6)$alkylene group;
Rc and Rd represent, independently of one another, a hydrogen atom or a $(C_1-C_6)$alkyl, aryl$(C_1-C_6)$alkylene or aryl group;
or Rc and Rd together form a $(C_2-C_5)$alkylene group;
Re represents a $(C_1-C_6)$alkyl, aryl$(C_1-C_6)$alkylene or aryl group;
or Rc and Re together form a $(C_2-C_5)$alkylene group;
Rf represents a hydroxyl, oxo, CHO or COOH group, or
   in the form of the base or of an addition salt with an acid.

2. The compound according to claim 1, wherein
R1 represents a phenyl group substituted by a halogen;
R2 and R3 represent, independently of one another, a hydrogen atom or a $(C_1-C_6)$alkyl group,
R4 represents a hydrogen atom or a $(C_1-C_6)$alkyl group;

X represents one or more hydrogen or halogen atoms, or X and R3 can form, together with the carbon atoms which carry them, a carbocycle of 5 carbon atoms; or in the form of the base or of an addition salt with an acid.

3. The compound according to claim 1, wherein
R1 represents a phenyl group substituted by a chlorine or a fluorine;
R2 and R3 represent, independently of one another, a hydrogen atom, a methyl or a cyclopropyl group;
R4 represents a hydrogen atom or a methyl group;
X represents one or more hydrogen or fluorine atoms, or X and R3 can form, together with the carbon atoms which carry them and with the benzofused ring, an indane group, or
in the form of the base or of an addition salt with an acid.

4. The compound according to claim 1, corresponding to the following formulae:
- {3-[2-(4-Chlorophenyl)pyrazolo[1,5-a]pyridin-5-yl]phenyl}methanol
- 2-{3-[2-(4-Chlorophenyl)pyrazolo[1,5-a]pyridin-5-yl]phenyl}propan-2-ol
- 1-{3-[2-(4-Chlorophenyl)pyrazolo[1,5-a]pyridin-5-yl]phenyl}ethanol
- 1-{3-[2-(4-Chlorophenyl)pyrazolo[1,5-a]pyridin-5-yl]phenyl}cyclopropylmethanol
- {3-[2-(4-Chlorophenyl)pyrazolo[1,5-a]pyridin-5-yl]-2,6-difluorophenyl}methanol
- {3-[2-(4-Fluorophenyl)pyrazolo[1,5-a]pyridin-5-yl]phenyl}methanol
- 2-{3-[2-(4-Fluorophenyl)pyrazolo[1,5-a]pyridin-5-yl]phenyl}propan-2-ol
- 1-{3-[2-(4-Fluorophenyl)pyrazolo[1,5-a]pyridin-5-yl]phenyl}ethanol
- 2-(4-Chlorophenyl)-5-(3-methoxymethylphenyl)pyrazolo[1,5-a]pyridine
- {4-[2-(4-Chlorophenyl)pyrazolo[1,5-a]pyridin-5-yl]phenyl}methanol
- {2-[2-(4-Chlorophenyl)pyrazolo[1,5-a]pyridin-5-yl]phenyl}methanol
- 6-[2-(4-Chlorophenyl)pyrazolo[1,5-a]pyridin-5-yl]indan-1-ol 5. A pharmaceutical composition comprising the compound of claim 1 or an addition salt of said compound with a pharmaceutically acceptable acid.

6. The pharmaceutical composition of claim 5 further comprising at least one pharmaceutically acceptable excipient.

7. A compound having formula (IIb1)

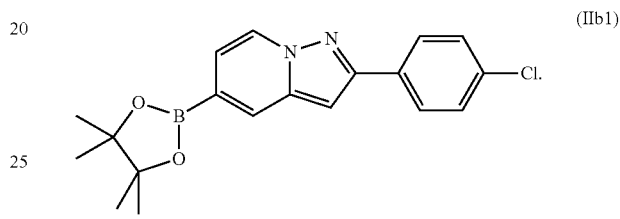

(IIb1)

* * * * *